United States Patent [19]

Maerzke et al.

[11] Patent Number: 4,995,380
[45] Date of Patent: Feb. 26, 1991

[54] PENILE PROSTHESIS

[75] Inventors: James T. Maerzke, Kenosha; Robert E. Trick, Racine, both of Wis.

[73] Assignee: Medical Engineering Corporation, Racine, Wis.

[21] Appl. No.: 433,052

[22] Filed: Nov. 7, 1989

[51] Int. Cl.$^5$ ............................................. A61F 2/26
[52] U.S. Cl. .................................................. 128/79
[58] Field of Search ........................................ 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,204,530 | 5/1980 | Finney | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,424,807 | 1/1984 | Evans, Sr. | 128/79 |
| 4,449,520 | 5/1984 | Palomar et al. | 128/79 |
| 4,550,719 | 11/1985 | Finney et al. | 128/79 |
| 4,550,720 | 11/1985 | Trick | 128/79 |
| 4,572,168 | 2/1986 | Fischell | 128/79 |
| 4,574,792 | 3/1986 | Trick | 128/79 |
| 4,590,927 | 5/1986 | Porter | 128/79 |
| 4,594,997 | 6/1986 | Hakky | 128/79 |
| 4,596,242 | 6/1986 | Fischell | 128/79 |
| 4,622,958 | 11/1986 | Finney | 128/79 |
| 4,682,589 | 7/1987 | Finney | 128/79 |
| 4,718,410 | 1/1988 | Hakky | 128/79 |
| 4,726,360 | 2/1988 | Trick et al. | 128/79 |

Primary Examiner—Cary E. Stone
Attorney, Agent, or Firm—Quarles & Brady

[57] ABSTRACT

A penile prosthesis consists of a pair of inflatable penile implants which each having a cylindrical body which contains a hydraulic system including a pressure chamber, a reservoir for pressurizing fluid, and a pump for transferring fluid under pressure to the pressure chamber to make it rigid. Each implant also contains a longitudinally compressible, but radially incompressible bellows in the reservoir which expands when the reservoir is empty and prevents the reservoir wall from collapsing. In one embodiment, a tube extends from the pump in the tip to the reservoir at the rear through the pressure chamber and there is a restricted orifice through which fluid can bleed back into the reservoir from the pressure chamber thus automatically controlling the length of time that the pressure chamber is pressurized and rigid.

4 Claims, 2 Drawing Sheets

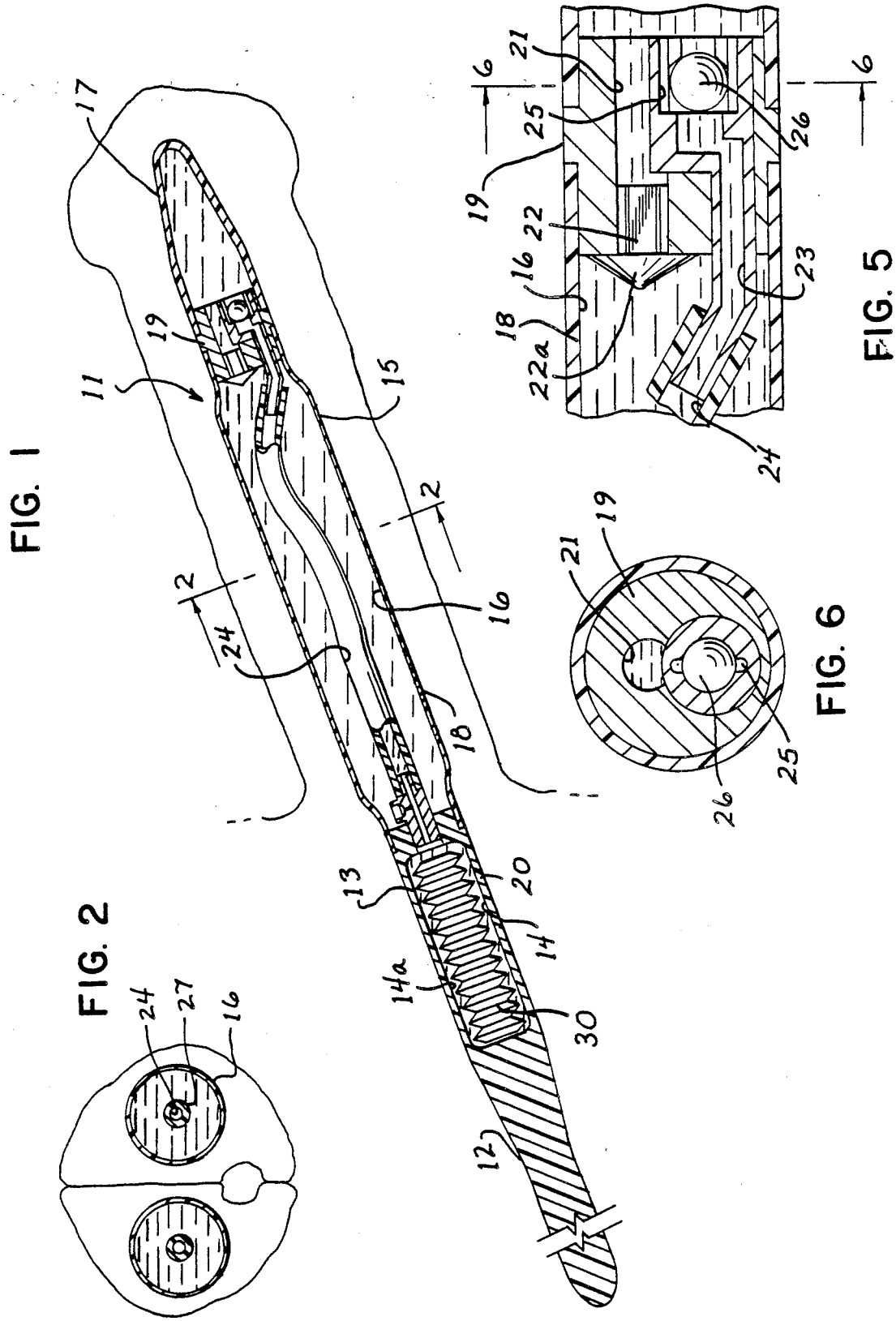

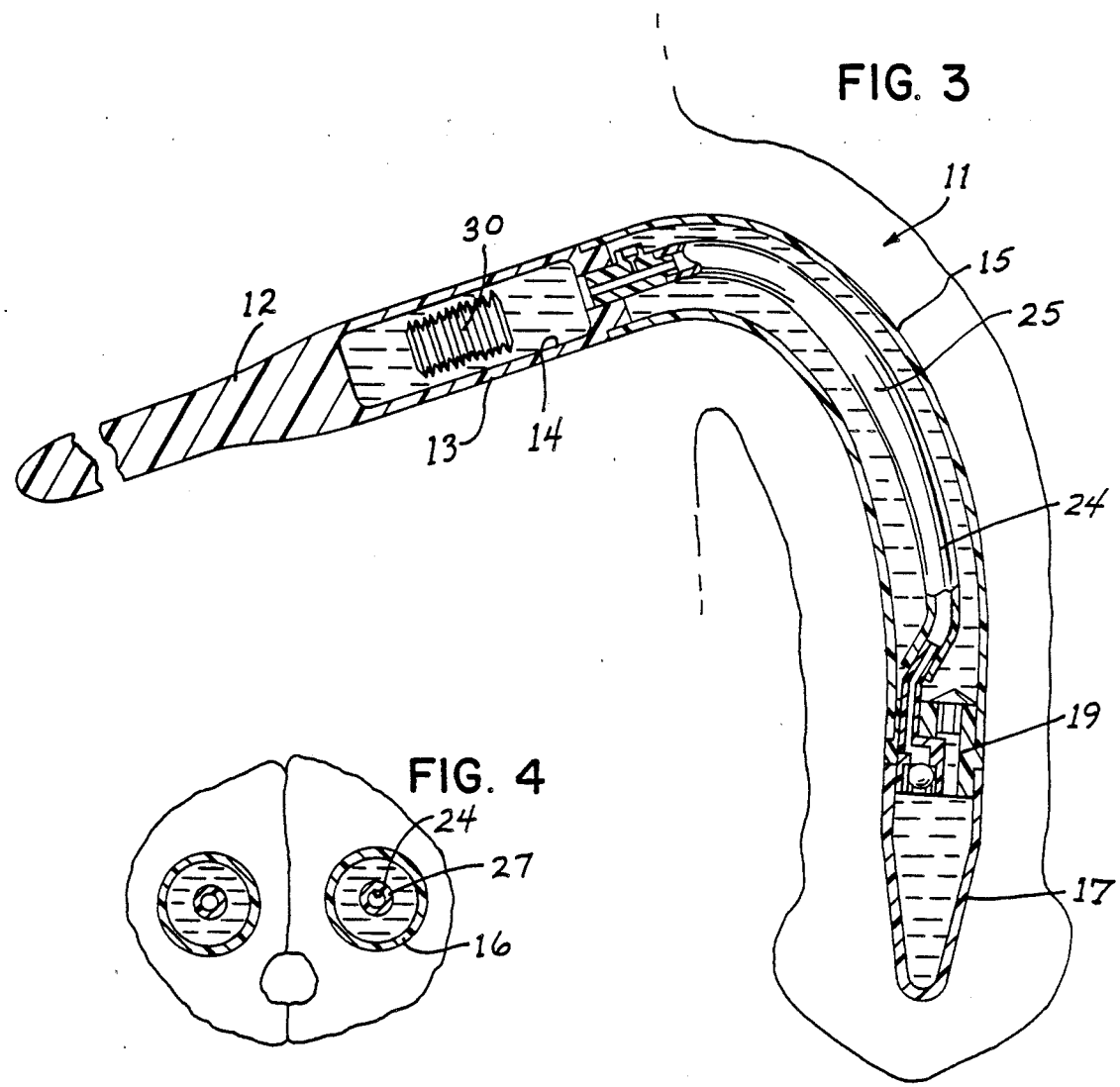
FIG. 3
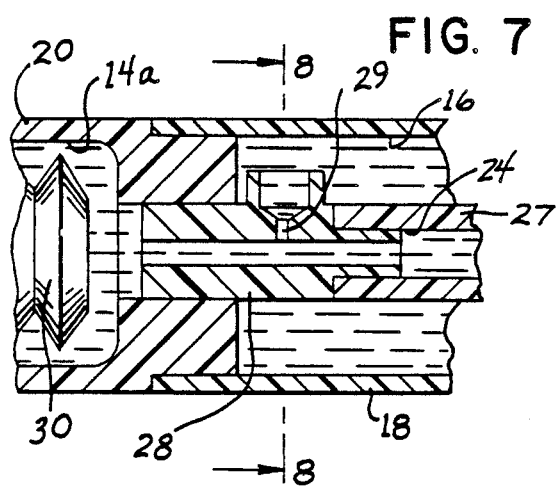
FIG. 4
FIG. 7
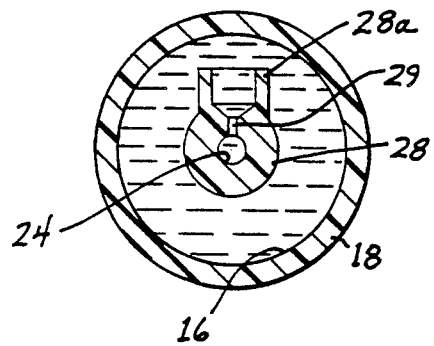
FIG. 8

PENILE PROSTHESIS

FIELD OF THE INVENTION

The present invention relates to a penile prosthesis. More particularly, it relates to an inflatable penile prosthesis which is adapted to be implanted in man for treatment of erectile impotence.

BACKGROUND OF THE INVENTION

There are instances of erectile impotence in which the patient does not respond to more conventional therapy and the surgical implanting of a penile prosthesis may be the only practical means of remedying the impotency.

Several types of penile prostheses have been employed in the past. One type of penile prosthesis is a pair of rods of suitable stiffness which are surgically implanted into the corpus cavernosum of the penis. One disadvantage of some of the rod-type implants is the permanent stiffness of the rod which can be a source of physical pain and/or embarrassment to the patient. The prostheses disclosed in U.S. Pat. No. 3,893,456 and U.S. Pat. No. 4,066,073 are representatives of the rod type prostheses.

Another type of penile prosthesis which is available is the inflatable prosthesis of U.S. Pat. No. 3,954,102. The patented prosthesis includes two fairly long inflatable and distensible tubes that are surgically implanted in the corpus cavernosum of the penis. Each of the two tubes is connected by tubing to a pressure bulb of inflating fluid which is implanted elsewhere in the body. Because of the volume required to inflate, distend, pressurize and rigidize the inflatable tubes, the pressure bulbs can be relatively large.

Recently penile implants have been patented which are cylinders systems which are adapted to be implanted in the corpora of the pendulous penis. These cylinders each contain a hydraulic system consisting of a pressure chamber, a reservoir for pressurizing fluid and a pump for transferring the fluid from the reservoir to the pressure chamber to make it rigid. Representative of such implants are those of U.S. Pat. Nos. 4,353,360, 4,267,829 and 4,383,525.

Although the previously patented prostheses are useful and valuable devices, there is still a need for improved penile implants.

SUMMARY OF THE INVENTION

It is the general object of the present invention to disclose an improved penile prosthesis.

The penile prosthesis of the present invention comprises a pair of novel penile implants. Each of the implants is an elongated cylindrical member which is adapted to be implanted into a separate corpus cavernosum in the penis. The cylinder includes a proximal portion for implanting in the root end of the corpus; an elongated flexible, hollow distal portion which contains a pressure chamber of limited distensibility and which is adapted to be implanted in the portion of the corpus cavernosum in the pendulus penis; and, an intermediate portion which includes a reservoir for pressurizing fluid to fill and pressurize the pressure chamber to make the distal portion rigid and to stiffen the penis. The cylinder also contains pump means for transferring the fluid from the reservoir to the pressure chamber.

The implants of the present invention differ from prior art implants in that the proximal reservoirs contain a gas-filled, longitudinally compressible, but radially incompressible bellows which fits closely within and substantially fills the proximal reservoir when the pressure chamber is pressurized. When the pressure chamber is not pressurized, the bellows is maintained in a longitudinally compressed state by a negative pressure or vacuum within the bellows. The bellows because it is radially incompressible prevents the walls of the reservoir from collapsing when the reservoir is emptied of fluid as occurs with prior art devices.

In a preferred embodiment, the pump means is located in the distal tip, the reservoir is located in the proximal stem and a tubular passage extends from the pump through the pressure chamber to the reservoir. The implant includes a valve means which connects the pressure chamber to the reservoir via the tubular passage. It permits fluid to bleed slowly back from the pressurized pressure chamber to the reservoir thereby automatically controlling the length of time required to convert the implant from being rigid to being flaccid and making manual depressurization unnecessary.

BRIEF DESCRIPTION OF THE DRAWINGS

In the drawings:

FIG. 1 is a side view, partly in section, of a preferred embodiment of the penile implant of the present invention. One of the two identical penile implants is shown surgically implanted in a male and in a pressurized condition;

FIG. 2 is an enlarged sectional view taken along lines 2—2 in FIG. 1;

FIG. 3 is a side view similar to FIG. 1, showing the pressure chamber depressurized;

FIG. 4 is an enlarged sectional view taken along line 4—4 in FIG. 3;

FIG. 5 is an enlarged sectional view of the valve between the pump and the pressure chamber in the embodiment of FIG. 1; and, FIG. 6 is a view, taken along line 6—6 in FIG. 5;

FIG. 7 is an enlarged sectional view of the bleed back valve in the embodiment of FIG. 1; and FIG. 8 is a view taken along line 8—8 in FIG. 7.

THE INVENTION

The preferred penile erectile system, which is shown in FIGS. 1–8, comprises a pair of cylindrical penile implants which are to be implanted in the corpora cavernosa of the penis. The two implants are identical, therefore, only one will be described in detail.

As seen in FIGS. 1 and 3 of the drawings, the implant 11 is a generally cylindrical member with a short proximal stem 12, an intermediate portion 13 including a fluid reservoir 14, and a longer distal portion 15 containing a pressure chamber 16 and a pump 17. The stem 12 which is of a relatively stiff material is implanted in the root end of a corpus cavernosum. The reservoir 14 is implanted in the portion of the corpus near the junction of the penis with the body and the pressure chamber 16 and the pump 17 are implanted in the portion of the corpus in the pendulous penis. Each of the two implants is positioned in a separate corpus cavernosum of the penis.

The pressure chamber 16 of the implant 11 has a cylindrical wall 18 of a flexible, non-distensible material so that the chamber 16 does not expand significantly in volume when pressurized but instead becomes stiff and rigid. The wall 18 is preferably of a material such as reinforced silicone rubber or polyurethane which either does not stretch or stretches only a given amount.

One end of cylindrical wall 18 is sealed to the distal end of the proximal stem 12. The other end of wall 18 is sealed to a valve block 19. The necessary fluid tight seals between the wall 18, the stem 12 and the valve block 19 may be made with a silicone adhesive or by other suitable means.

The reservoir 14 also has a wall 20 which is non-distensible. It is preferably relatively thicker and less flexible than the wall 18.

When the pressure chamber 16 of the implant 11 is pressurized, as seen in FIGS. 1 and 2, the penis assumes an erectile position. The distal portion 15 is then rigid as a result of the chamber 16 being completely filled with fluid under pressure.

When the implant 11 is in a nonpressurized state as seen in FIGS. 3 and 4, the chamber 16 is substantially filled with a non-compressible hydraulic fluid (not seen) which is biocompatible, such as saline or a free flowing silicone gel. In the non-pressurized state, the distal portion 15, including chamber 16, flexes and permits the penis to assume a substantially normal, flaccid position.

The means for transferring fluid from the reservoir 14 to the chamber 16 and the various means for controlling fluid flow between the various components of the implant 11 will now be described.

As seen best in FIGS. 1 and 3, the means for transferring fluid to the pressure chamber 16 is the pump 17 which is positioned in the tip of the distal portion 15.

The valve block 19 is positioned between the pump 17 and the pressure chamber 16. It contains the valves which control the fluid flow between the pump 17 and the pressure chamber 16 and the reservoir 14 and the pump 17, respectively.

As seen best in FIGS. 5 and 6, the valve block 19 includes a passage 21 which leads from the pump 17 to the pressure chamber 16. A valve 22 having an umbrella shaped head 22a normally prevents the flow of fluid through the passage 21. The valve 22 is normally kept closed by fluid pressure in the pressure chamber 16; however, it can be opened by squeezing the walls of the pump 17 to force liquid through the passage 21 to unseat the edges of the umbrella shaped head 22a and create flow passages. A second passage 23 also extends through the valve block 21. It leads from the pump 17 to a tubular passage 24 which leads to the reservoir 14. The passage 23 has an enlarged portion 25 in which a ball 26 is seated. The ball 26 closes the passage 23 when the pump 17 is squeezed and opens it to fluid flow from the reservoir 14 via the tubular passage 24 when the walls of the pump 17 assume their normal state and the interior of the pump 17 is at a lower pressure than the reservoir 14.

As seen best in FIGS. 1, 3 and 7, the reservoir 14 has a bore 14a in which a longitudinally compressible, but radially incompressible, gas-filled bellows 30 is positioned. The bellows 30 has an outside diameter which approximates that of the bore 14a and the radially incompressible expanded bellows 30 prevents the wall 20 of the reservoir 14 from collapsing when the reservoir 14 is emptied as seen in FIG. 1. The bellows 30 is preferably made of metal or plastic. The internal pressure of the gas in the bellows 30 which is about 0 to 2 psi absolute when compressed is enough to assist it to expand the bellows longitudinally to fill the reservoir 14 when it is emptied by the pump. The selected pressure is also low enough to so that the bellows 30 is readily compressed by the fluid returning to the reservoir 14 as the pressure chamber 16 is being depressurized as seen in FIG. 3.

Turning to FIGS. 1, 3, 7 and 8, it can be seen that the tubular passage 24 comprises a tube 27 and a T-shaped connector 28 which connects the tube 27 to the reservoir 14. The stem 28a of the connector 28 includes a restricted opening 29. When the pressure chamber 16 is pressurized fluid will slowly flow back from the relatively higher pressured chamber 16 to the lower pressured reservoir 14 via the restricted orifice 29 and the tubular passage 24. When sufficient fluid has been transferred back to the reservoir 14, the pressure chamber 16 and the distal portion 15 of the implant become soft, and the penis again assumes the flaccid state seen in FIG. 3. The size of restricted opening 29 is selected so that the erection lasts for a predetermined time and it eliminates the need to manually depressurize the pressure chamber.

The term "substantially filled" as used herein to describe the fluid content of a chamber in the penile implant 11 means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

The term "limited distensibility" as used herein is intended to cover materials or components which do not distend or distend to only a limited extent which still permits the device to function as intended.

All the components of the described implants are made of biocompatible materials having the necessary properties to function as intended. In the preferred embodiment, all the parts and components of the prosthesis are made of or covered with medical grade silicone rubber which is non-reactive, non-toxic and well tolerated by the adjacent organic tissues Silicone rubber is preferred because it is quite resistant to wear and remains functional for long period of time. However, other suitable materials possessing desirable properties may also be employed.

The preferred method of implantation of the prosthesis of the present invention is through an incision made in the penis. After appropriate incision, each corpus cavernosum is dilated distally and proximally to accept the implants. The appropriate anatomical measurements are made to insure that the proximal end of the implant or implants will be positioned is the proximal crus. An appropriately sized implant is then inserted into the corpus cavernosum of the penis. The distal tip is positioned in the glans end of the corpus cavernosum. The stem at the proximal end of the implant is anchored in the root end of the corpus cavernosum.

The identical procedure is performed on the other side of the penis to complete the surgical procedure. The stems of the two implants preferably will diverge laterally to accommodate the anatomy, to provide lateral stability to the penis and to help prevent rotation of the implants. The incision is then closed.

It will be understood that the foregoing description has been for purposes of illustration, and a number of changes may be made without departing from the spirit and scope of the invention. Therefore, the invention is not to be limited except by the claims which follow.

We claim:

1. In a penile implant comprising a cylindrical member containing a pressure chamber, a reservoir for pressurizing fluid and means operatively connected between the reservoir and the pressure chamber for transferring fluid into the pressure chamber from the reservoir, the improvement in which the reservoir contains a longitudinally compressible and radially incompressible member which expands and prevents the reservoir wall from collapsing when the pressurizing fluid in the reservoir is transferred to the pressure chamber.

2. An implant of claim 1 in which the longitudinally compressible and radially incompressible member is a gas filled bellows.

3. In a penile implant comprising a cylindrical member containing a pressure chamber, a proximal reservoir for pressurizing fluid and pump means in the distal tip for transferring fluid to the pressure chamber from the reservoir, the improvement which comprises a tubular passage which extends through the pressure chamber and connects the pump means to the reservoir, said passage including bleed valve means for automatically depressurizing the pressure chamber.

4. An implant of claim 3 in which the bleed valve means is a restricted orifice through which fluid in the pressure chamber can flow via the tubular member back into the reservoir thereby depressurizing the pressure chamber.

* * * * *